United States Patent
Kyle et al.

(10) Patent No.: US 7,678,809 B2
(45) Date of Patent: Mar. 16, 2010

(54) BENZIMIDAZOLE COMPOUNDS HAVING NOCICEPTIN RECEPTOR AFFINITY

(75) Inventors: Donald Kyle, Newtown, PA (US); Richard R. Goehring, Pipersville, PA (US); Bin Shao, Richboro, PA (US)

(73) Assignee: Purdue Pharma L.P., Stamford, CT (US)

( * ) Notice: Subject to any disclaimer, the term of this patent is extended or adjusted under 35 U.S.C. 154(b) by 220 days.

(21) Appl. No.: 11/494,826

(22) Filed: Jul. 28, 2006

(65) Prior Publication Data

US 2006/0264638 A1    Nov. 23, 2006

Related U.S. Application Data

(63) Continuation of application No. 09/730,934, filed on Dec. 6, 2000.

(60) Provisional application No. 60/169,394, filed on Dec. 6, 1999.

(51) Int. Cl.
*A61K 31/44*    (2006.01)
(52) U.S. Cl. .................................... 514/300
(58) Field of Classification Search .................. 514/322, 514/300
See application file for complete search history.

(56) References Cited

U.S. PATENT DOCUMENTS

| | | | |
|---|---|---|---|
| 3,161,645 A | 12/1964 | Adrian et al. | 260/293.4 |
| 3,196,157 A | 7/1965 | Janssen et al. | |
| 3,318,900 A | 5/1967 | Adrian et al. | 260/294 |
| 4,329,353 A | 5/1982 | Stokbroekx et al. | 424/267 |
| 6,262,066 B1 * | 7/2001 | Tulshian et al. | 514/299 |
| 6,455,527 B2 * | 9/2002 | Tulshian et al. | 514/249 |
| 2003/0073690 A1 * | 4/2003 | Tulshian et al. | 514/248 |

FOREIGN PATENT DOCUMENTS

| | | |
|---|---|---|
| EP | 0008259 | 2/1980 |
| EP | 0092391 (A2) | 10/1983 |
| EP | 0921125 (A1) | 6/1999 |
| WO | 9710213 | 3/1997 |
| WO | 9740035 | 10/1997 |
| WO | 9854168 | 12/1998 |
| WO | 9929696 | 6/1999 |
| WO | 9936421 | 6/1999 |
| WO | 9948492 | 9/1999 |
| WO | 9959997 | 11/1999 |
| WO | 0006545 | 2/2000 |

OTHER PUBLICATIONS

USPatfull Abstract 2001:107097.*
Hcaplus 1998:644540.*
Obase, et al., "New Antihypertensive Agents. I. Synthesis and Antihypertensive Activity of Some 4-Piperidylbensimidasolinone Derivatives", Chemical Pharmaceutical Bulletin, vol. 30, pp. 462-473, 1982.

* cited by examiner

*Primary Examiner*—Janet L Andres
*Assistant Examiner*—Binta M Robinson
(74) *Attorney, Agent, or Firm*—Davidson, Davidson & Kappel, LLC

(57) ABSTRACT

Disclosed are compounds of the formula (I)

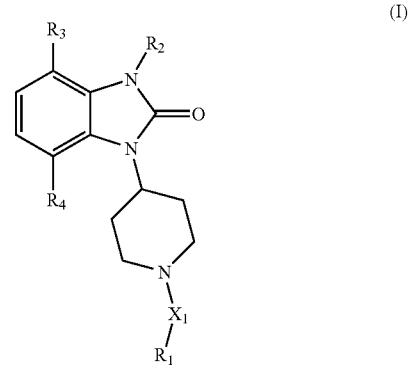

wherein A, $R_1$, $R_2$, $R_3$, $R_4$ and $X_1$ are as disclosed herein. The compounds have affinity for the ORL1 receptor and are useful in the treatment of chronic and acute pain.

15 Claims, No Drawings

BENZIMIDAZOLE COMPOUNDS HAVING NOCICEPTIN RECEPTOR AFFINITY

This application is a continuation of U.S. application Ser. No. 09/730,934, filed Dec. 6, 2000, which claims the benefit of U.S. provisional No. 60/169,394 filed Dec. 6, 1999, the disclosure of which is hereby incorporated by reference.

BACKGROUND OF THE INVENTION

Chronic pain is a major contributor to disability in the industrialized world and is the cause of an untold amount of suffering. The successful treatment of severe and chronic pain is a primary goal of the physician with opioid analgesics being the current drugs of choice. Unfortunately, this class of compounds produces several undesirable side effects including respiratory depression, constipation, and the development of tolerance and dependence.

Opioids are derived from the opium poppy *papaya somniferum* and include drugs such as morphine, codeine and semi-synthetic compounds derived from them and from thebaine, another component of the opium poppy. It was hypothesized that the opioids derived their therapeutic effect by interacting with specific receptor sites in the body. Later experiments led to the belief that there were more than one receptor site in the body, in explanation for the fact that the synthetic compound nalorphine provides analgesic activity while at the same time, antagonizes the analgesic effect of morphine.

Until recently, there was evidence of three major classes of opioid receptors in the central nervous system (CNS), with each class having subtype receptors. These receptor classes were designated as $\mu$, $\delta$ and k. As opiates had a high affinity to these receptors while not being endogenous to the body, research followed in order to identify and isolate the endogenous ligands to these receptors. These ligands were identified as enkephalins, endorphins and dynorphins.

Recent experimentation has led to the identification of a cDNA encoding an opioid receptor-like (ORL1) receptor with a high degree of homology to the known receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and k receptors had low affinity for the ORL1. This characteristic, along with the fact that an endogenous ligand had not yet been discovered, led to the term "orphan receptor".

Subsequent research led to the isolation and structure of the endogenous ligand of the ORL1 receptor. This ligand is a seventeen amino acid peptide structurally similar to members of the opioid peptide family The discovery of the ORL1 receptor presents an opportunity in drug discovery for novel compounds which can be administered for pain management or other syndromes modulated by this receptor.

Given the close structural homology of ligands to the ORL1 receptor to ligands of the other opioid receptors, such drug discovery could also lead to compounds having a higher affinity for the $\mu$, $\delta$ and k receptors than known compounds, while producing less side effects.

OBJECTS AND SUMMARY OF THE INVENTION

It is accordingly an object of the present invention to provide new compounds which exhibit affinity for the ORL1 receptor.

It is another object of the present invention to provide new compounds which exhibit affinity for the ORL1 receptor and one or more of the $\mu$, $\delta$ or k receptors.

It is another object of the present invention to provide new compounds for treating a patient suffering from chronic or acute pain by administering a compound having affinity for the ORL1 receptor.

It is another object of the invention to provide new compounds which have agonist activity at the $\mu$, $\delta$ and k receptors which is greater than compounds currently available e.g. morphine.

It is another object of the invention to provide methods of treating chronic and acute pain by administering compounds which have agonist activity at the $\mu$, $\delta$ and k receptors which is greater than compounds currently available.

It is another object of the invention to provide methods of treating chronic and acute pain by administering non-opioid compounds which have agonist activity at the $\mu$, $\delta$ and k receptors and which produce less side effects than compounds currently available.

It is another object of the present invention to provide compounds useful as analgesics, antiinflammatories, diuretics, anesthetics and neuroprotective agents and methods for administering said compounds.

It is another object of the present invention to provide a method of modulating a response from opioid receptors comprising administering a compound having a binding affinity for the ORL1 receptor of less than 500 $K_i$ (nM) and a binding affinity for the mu receptor of less than 25 $K_i$ (nM).

It is another object of the invention to provide a method of reducing side effects associated with the administration of opioid analgesics in a human patient comprising administering to a human patient an analgesically effective amount of a non-opioid compound which exhibits a binding affinity for the ORL1 receptor of less than 500 $K_i$ (nM). In other embodiments, the compound has a binding affinity for the mu receptor of less than 25 $K_i$ (nM).

Other objects and advantages of the present invention will become apparent from the following detailed description thereof. With the above and other objects in view, the present invention in certain embodiments comprises compounds having the general formula (I):

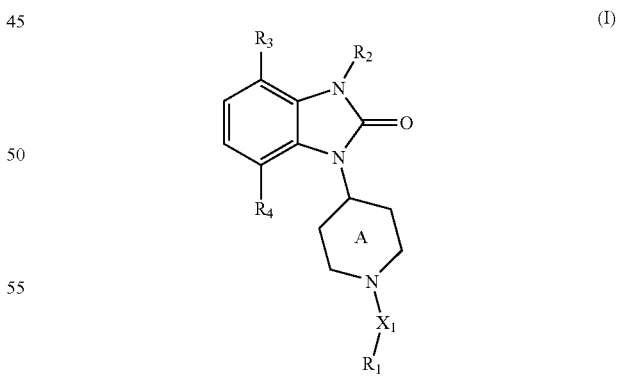

wherein

A is a saturated, unsaturated or partially unsaturated ring $X_1$ is selected from the group consisting of a bond, $C_{1-10}$ branched or straight alkyl, alkenyl, alkynylene optionally substituted with 1-3 halogen, oxo or phenyl groups, said phenyl group optionally substituted with 1-3 halogen or $C_{1-10}$ alkyl groups;

$R_1$ is selected from the group consisting of hydrogen, $C_{3-12}$ cycloalkyl, $C_{3-12}$ cycloalkenyl, a monocyclic, bicyclic or tricyclic aryl or heteroaryl ring, a heteromonocyclic ring, and a heterobicyclic ring system, wherein said $C_{3-12}$ cycloalkyl, $C_{3-12}$ cycloalkenyl, monocyclic, bicyclic or tricyclic aryl or heteroaryl ring, heteromonocyclic ring, and heterobicyclic ring system are optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl;

$R_2$ is selected from the group consisting of $C_{1-10}$ alkyl, $C_{3-12}$ cycloalkyl and halogen, said alkyl and cycloalkyl substituted with an oxo group; and $R_3$ and $R_4$ are independently selected from the group consisting of hydrogen, hydroxy, $C_{1-3}$ alkyl, $C_{1-3}$ alkoxy, $C_{1-3}$ carbonyl and halogen; and pharmaceutically acceptable salts thereof.

In preferred embodiments, A has one double bond at the 1,2 position.

In preferred embodiments, $X_1R_1$ is not hydrogen.

In preferred embodiments, A has one double bond at the 1,2 position.

In other preferred embodiments $X_1$ is selected from a bond, methyl, ethyl or propyl.

In other preferred embodiments $X_1$ is substituted with fluorophenyl.

In other preferred embodiments $R_1$ is a tricyclic aryl ring, preferably dibenzocycloheptyl.

In other preferred embodiments $R_1$ is a cycloalkyl, preferably cyclopentyl, cyclohexyl or cycloheptyl, wherein the cycloalkyl is optionally substituted with a $C_{1-3}$ alkyl.

In other preferred embodiments $R_1$ is a monocyclic aryl ring, preferably phenyl, wherein the aryl ring is optionally substituted with a halogen, $C_{1-3}$ alkyl, phenyl or benzyloxy.

In other preferred embodiments, $R_1$ is selected from napthyl, benzyloxyphenyl, decahydronaphyl, 1,3 hydro-indene, propylhexane, cyclodecyl, biphenylmethyl, phenylethyl, cyclooctyl, 1,2,3,4,hydro-napthyl, 1-3 dimethyl-pentyl.

In other preferred embodiments, $R_2$ is a methyl, ethyl or propyl wherein the methyl ethyl and propyl are optionally substituted with an oxo group.

In other preferred embodiments, $R_3$ and $R_4$ are both hydrogen.

As used herein, the term "alkyl" means a linear or branched saturated aliphatic hydrocarbon group having a single radical and 1-10 carbon atoms. Examples of alkyl groups include methyl, propyl, isopropyl, butyl, n-butyl, isobutyl, sec-butyl, tert-butyl, and pentyl. A branched alkyl means that one or more alkyl groups such as methyl, ethyl or propyl, replace one or both hydrogens in a —$CH_2$— group of a linear alkyl chain.

The term "cycloalkyl" means a non-aromatic mono- or multicyclic hydrocarbon ring system having a single radical and 3-12 carbon atoms. Exemplary monocyclic cycloalkyl rings include cyclopropyl, cyclopentyl, and cyclohexyl. Exemplary multicyclic cycloalkyl rings include adamantyl and norbornyl.

The term "alkenyl" means a linear or branched aliphatic hydrocarbon group containing a carbon-carbon double bond having a single radical and 2-10 carbon atoms. A "branched" alkenyl means that one or more alkyl groups such as methyl, ethyl or propyl replace one or both hydrogens in a —$CH_2$— or —CH= linear alkenyl chain. Exemplary alkenyl groups include ethenyl, 1- and 2-propenyl, 1-, 2- and 3-butenyl, 3-methylbut-2-enyl, 2-propenyl, heptenyl, octenyl and decenyl.

The term "cycloalkenyl" means a non-aromatic monocyclic or multicyclic hydrocarbon ring system containing a carbon-carbon double bond having a single radical and 3 to 12 carbon atoms. Exemplary monocyclic cycloalkenyl rings include cyclopropenyl, cyclopentenyl, cyclohexenyl or cycloheptenyl. An exemplary multicyclic cycloalkenyl ring is norbornenyl.

The term "aryl" means a carbocyclic aromatic ring system containing one, two or three rings which may be attached together in a pendent manner or fused, and containing a single radical. Exemplary aryl groups include phenyl and naphthyl.

The term "heterocyclic" means cyclic compounds having one or more heteroatoms (atoms other than carbon) in the ring, and having a single radical. The ring may be saturated, partially saturated and unsaturated, and the heteroatoms may be selected from the group consisting of nitrogen, sulfur and oxygen. Examples of saturated heterocyclic radicals include saturated 3 to 6-membered heteromonocyclic groups containing 1 to 4 nitrogen atoms, such as pyrrolidinyl, imidazolidinyl, piperidino, piperazinyl; saturated 3- to 6-membered heteromonocyclic groups containing 1 to 2 oxygen atoms and 1 to 3 nitrogen atoms, such as morpholinyl; saturated 3- to 6-membered heteromonocyclic groups containing 1 to 2 sulfur atoms and 1 to 3 nitrogen atoms, such as thiazolidinyl. Examples of partially saturated heterocyclic radicals include dihydrothiophene, dihydropyran, and dihydrofuran.

The term "heteroaryl" means unsaturated heterocyclic radicals, wherein heterocyclic is as previously described. Exemplary heteroaryl groups include unsaturated 3 to 6 membered heteromonocyclic groups containing 1 to 4 nitrogen atoms, such as pyrrolyl, pyridyl, pyrimidyl, and pyrazinyl; unsaturated condensed heterocyclic groups containing 1 to 5 nitrogen atoms, such as indolyl, quinolyl, isoquinolyl; unsaturated 3 to 6-membered heteromonocyclic groups containing an oxygen atom, such as furyl; unsaturated 3 to 6 membered heteromonocyclic groups containing a sulfur atom, such as thienyl; unsaturated 3 to 6 membered heteromonocyclic groups containing 1 to 2 oxygen atoms and 1 to 3 nitrogen atoms, such as oxazolyl; unsaturated condensed heterocyclic groups containing 1 to 2 oxygen atoms and 1 to 3 nitrogen atoms, such as benzoxazolyl; unsaturated 3 to 6 membered heteromonocyclic groups containing 1 to 2 sulfur atoms and 1 to 3 nitrogen atoms, such as thiazolyl; unsaturated condensed heterocyclic group containing 1 to 2 sulfur atoms and 1 to 3 nitrogen atoms, such as benzothiazolyl. The term "heteroaryl" also includes unsaturated heterocyclic radicals, wherein heterocyclic is as previously described, in which the heterocyclic group is fused with an aryl group, in which aryl is as previously described. Exemplary fused radicals include benzofuran, benzodioxole and benzothiophene.

As used herein, the term "patient" includes both human and other mammals.

As used herein, the term "halogen" includes fluoride, bromide, chloride, iodide or alabamide.

The invention disclosed herein is meant to encompass all pharmaceutically acceptable salts thereof of the disclosed compounds. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparaginate, glutamate and the like.

The invention disclosed herein is also meant to encompass all prodrugs of the disclosed compounds. Prodrugs are considered to be any covalently bonded carriers which release the active parent drug in vivo.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Some of the compounds disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

Certain preferred compounds of formula I according to the invention include:

1-[1-dibenzocycloheptyl-4-piperidinyl]-3-[1-oxo-ethyl]-1, 3-dihydro-2H-1,3-benzamidazol-2-one;

1-[1-(4-propylcyclohexane)-4-piperidinyl]-3-[1-oxo-propyl]-1,3-dihydro-2H-1,3-benzamidazol-2-one;

1-[1-(4-propylcyclohexane)-4-piperidinyl]-3-[1-oxo-ethyl]-1,3-dihydro-2H-1,3-benzamidazol-2-one;

1-[1-(4-propylcyclohexane)-4-piperidinyl]-3-[2-oxo-cyclopropyl]-1,3-dihydro-2H-1,3-benzamidazol-2-one;

1-[1-(4-propyl-1,2-cyclohexene)-4-piperidinyl-3-[1-oxo-ethyl]-1,3-dihydro-2H-1,3-benzamidazol-2-one;

1-[1-(4,4-difluorophenylbutyl)-4-piperidinyl]-3-[1-oxo-ethyl]-1,3-dihydro-2H-1,3-benzamidazol-2-one; and 1-[1-(4-phenyl-phenylmethyl)-4-piperidinyl]-3-[1-oxo-ethyl]-1,3-dihydro-2H-1,3-benzamidazol-2-one.

1-[1-(2-napthyl-methyl)-4-piperidinyl]-3-[1-oxo-ethyl]-1,3-dihydro-2H-1,3-benzamidazol-2-one;

1-[1-(4-benzyloxy-benzyl)-4-piperidinyl]-3-[1-oxo-ethyl]-1,3-dihydro-2H-1,3-benzamidazol-2-one;

1-[1-(decahydronaphyl)-4-piperidinyl]-3-[1-oxo-ethyl]-1,3-dihydro-2H-1,3-benzamidazol-2-one;

1-[1-(2[1,3 dihydro-indene])-4-piperidinyl]-3-[1-oxo-ethyl]-1,3-dihydro-2H-1,3-benzamidazol-2-one;

1-[1-(4-isopropylhexane)-4-piperidinyl]-3-[1-oxo-ethyl]-1, 3-dihydro-2H-1,3-benzamidazol-2-one;

1-[1-(4-[1-methyl-ethyl]hexane)-4-piperidinyl]-3-[1-oxo-ethyl]-1,3-dihydro-2H-1,3-benzamidazol-2-one;

1-[1-cyclodecyl-4-piperidinyl]-3-[1-oxo-ethyl]-1,3-dihydro-2H-1,3-benzamidazol-2-one;

1-[1-(3-diphenylpropyl)-4-piperidinyl]-3-[1-oxo-ethyl]-1,3-dihydro-2H-1,3-benzamidazol-2-one;

1-[1-(2-phenylethyl)-4-piperidinyl]-3-[1-oxo-ethyl]-1,3-dihydro-2H-1,3-benzamidazol-2-one;

1-[1-(cyclooctylmethyl)-4-piperidinyl]-3-[1-oxo-ethyl]-1,3-dihydro-2H-1,3-benzamidazol-2-one;

1-[1-(4-[1,2,3,4,hydro-napthyl])-4-piperidinyl]-3-[1-oxo-ethyl]-1,3-dihydro-2H-1,3-benzamidazol-2-one;

1-[1-(4-[1-3 dimethyl-pentyl])-4-piperidinyl]-3-[1-oxo-ethyl]-1,3-dihydro-2H-1,3-benzamidazol-2-one; and pharmaceutically acceptable salts thereof.

The present invention is also directed to the following compounds:

1-[4-dibenzocycloheptyl-4-piperidinyl]-1,3-dihydro-2H-1, 3-benzamidazol-2-one;

1-[4-(4-propylcyclohexane)-4-piperidinyl]-1,3-dihydro-2H-1,3-benzamidazol-2-one;

1-[4-(4-propyl-1,2-cyclohexene)-4-piperidinyl-1,3-dihydro-2H-1,3-benzamidazol-2-one;

1-[4-(4,4-difluorophenylbutyl)-4-piperidinyl]-1,3-dihydro-2H-1,3-benzamidazol-2-one;

1-[4-(4-phenyl-phenylmethyl)-4-piperidinyl]-1,3-dihydro-2H-1,3-benzamidazol-2-one; and pharmaceutically acceptable salts thereof.

DETAILED DESCRIPTION OF THE INVENTION

The compounds of the present invention can be administered to anyone requiring modulation of the opioid and ORL1 receptors. Administration may be orally, topically, by suppository, inhalation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553B1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The following examples illustrate various aspects of the present invention, and are not to be construed to limit the claims in any manner whatsoever.

Example 1

1-[4-(4-propylcyclohexane)-4-piperidinyl]-3-[1-oxo-ethyl]-1,3-dihydro-2H-1,3-benzamidazol-2-one The above compound was synthesized according to the following synthetic scheme and general procedure:

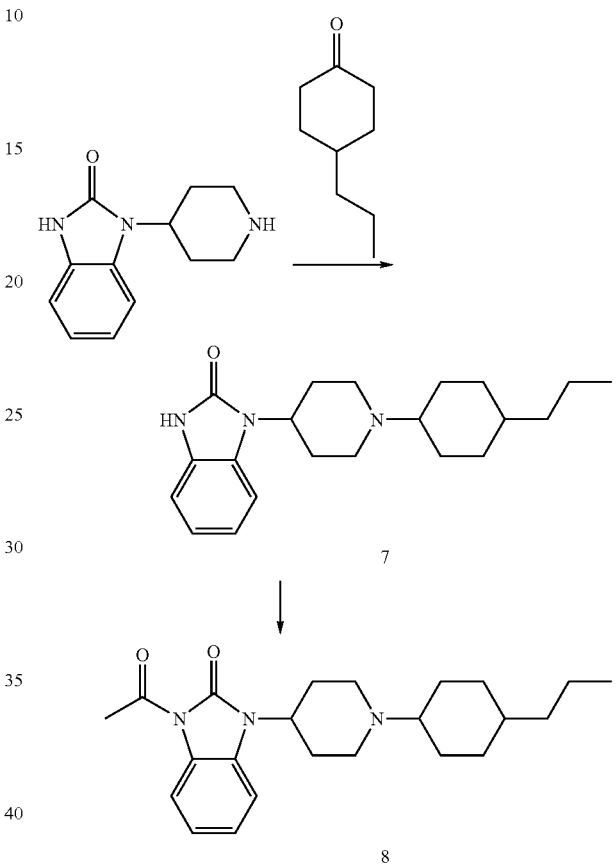

General Procedure for Reductive Coupling. A solution containing the amine and ketone in toluene was refluxed in the presence of molecular sieves for 5-6 hours. The reaction mixture was cooled and filtered through Celite and the Celite cake was washed with Dichloromethane. The combined filtrate was concentrated to dryness. The residue was dissolved in a mixture of THF and methanol (10:1). To the solution was then added 1 eq of NaCNBH3 in one portion and a few drops of acetic acid to adjust pH=4-5. The reaction was stirred at room temperature for 12 hours. The reaction mixture was diluted with EtOAc and washed with 1N NaOH solution. The aqueous was extracted with additional EtOAc and the combined organic was dried with MgSO4, filtered and concentrated. The desired product was purified either by recrystallization or flash chromatography on silica gel.

Preparation of Example 1

To a solution of 380 mg of example 1 in 10 ml dichloromethane was added 236 mg Et₃N, 99 mg acetyl chloride and a catalytic amount of DMAP. The reaction was stirred at room temperature for 12 hours. After diluting with dichloromethane the mixture was washed with brine and the aqueous phase extracted with additional dichloromethane. The combined organic extracts were dried over MgSO4, filtered and concentrated. The residue was purified via flash chromatography (silica, EtOAc) to give desired product.

1HNMR in CDCl$_3$ (ppm): 7.35 (t, 2H), 7.10 (m, 7H), 5.05 (s, 2H), 3.13-2.80 (m, 9H), 2.62 (s, 3H), 2.40 (m, 2H), 2.13 (m, 1H), 1.89 (bd, 2H), 1.70 (m, 1H). LCMS: 404 (M+1).

The general procedures disclosed above can be modified in order to synthesize the other preferred compounds of the invention.

Example 2

Nociceptin affinity at the ORL1 receptor for preferred compounds was obtained using the following assay:

Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 ml/10 cm dish) followed by homogenization with a tissue grinder/teflon pestle. Membranes were collected by centrifugation at 30,000×g for 15 min at 4° C. and pellets resuspended in hypotonic buffer to a final concentration of 1-3 mg/ml. Protein concentrations were determined using the BioRad protein assay reagent with bovine serum albumen as standard. Aliquots of the ORL-1 receptor membranes were stored at −80° C.

Functional SGTPγS binding assays were conducted as follows. ORL-1 membrane solution was prepared by sequentially adding final concentrations of 0.066 µg/µl ORL-1 membrane protein, 10 µg/ml saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µl/well) was transferred to 96-shallow well polypropylene plates containing 10 µl of 20× concentrated stock solutions of agonist prepared in DMSO. Plates were incubated for 30 min at room temperature with shaking. Reactions were terminated by rapid filtration onto 96-well Unifilter GF/B filter plates (Packard) using a 96-well tissue harvester (Brandel) and followed by three filtration washes with 200 µl ice-cold binding buffer (10 mM NaH$_2$PO$_4$, 10 mM Na$_2$HPO$_4$, pH 7.4). Filter plates were subsequently dried at 50° C. for 2-3 hours. Fifty µl/well scintillation cocktail (BetaScint; Wallac) was added and plates were counted in a Packard Top-Count for 1 min/well.

Data was analyzed using the curve fitting functions in GraphPad PRISM™, v. 3.0 and the results are set forth in table 1 below:

TABLE 1

Nociceptin Affinity

| Compound | calc K$_i$ (nM) |
|---|---|
| 1-[4-(4-propylcyclohexane)-4-piperidinyl]-1,3-dihydro-2H-1,3-benzamidazol-2-one | 394 |
| 1-[4-(4-propylcyclohexane)-4-piperidinyl]-3-[1-oxo-ethyl]-1,3-dihydro-2H-1,3-benzamidazol-2-one | 464 |
| 1-[4-(4-propylcyclohexane)-4-piperidinyl]-1,3-dihydro-2H-1,3-benzamidazol-2-one | 166 |
| 1-[4-(4-propyl-1,2-cyclohexene)-4-piperidinyl]-1,3-dihydro-2H-1,3-benzamidazol-2-one | 469 |
| 1-[4-(4,4-difluorophenylbutyl)-4-piperidinyl]-1,3-dihydro-2H-1,3-benzamidazol-2-one | 420 |
| 1-[4-(4-phenyl-phenylmethyl)-4-piperidinyl]-1,3-dihydro-2H-1,3-benzamidazol-2-one | 1252 |

Example 3

Affinity at the µ, k and δ receptors for preferred compounds was obtained according to the following assays:

Mu, kappa or delta opioid receptor membrane solution was prepared by sequentially adding final concentrations of 0.075 µg/µl of the desired membrane protein, 10 µg/ml saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µl/well) was transferred to 96-shallow well polypropylene plates containing 10 µl of 20× concentrated stock solutions of agonist prepared in DMSO. Plates were incubated for 30 min at room temperature with shaking. Reactions were terminated by rapid filtration onto 96-well Unifilter GF/B filter plates (Packard) using a 96-well tissue harvester (Brandel) and followed by three filtration washes with 200 µl ice-cold binding buffer (10 mM NaH$_2$PO$_4$, 10 mM Na$_2$HPO$_4$, pH 7.4). Filter plates were subsequently dried at 50° C. for 2-3 hours. Fifty µl/well scintillation cocktail (MicroScint20, Packard) was added and plates were counted in a Packard Top-Count for 1 min/well.

Data were analyzed using the curve fitting functions in GraphPad PRISM™, v. 3.0 and the results are set forth in table 2 below:

TABLE 2

| Compound | calc K$_i$ (nM) | | |
|---|---|---|---|
| | µ | k | δ$_2$ |
| 1-[4-(4-propylcyclohexane)-4-piperidinyl]-1,3-dihydro-2H-1,3-benzamidazol-2-one | 19 | 270 | >10,000 |
| 1-[4-(4-propylcyclohexane)-4-piperidinyl]-3-[1-oxo-ethyl]-1,3-dihydro-2H-1,3-benzamidazol-2-one | 23.2 | 1600 | >10,000 |
| 1-[4-(4-propylcyclohexane)-4-piperidinyl]-1,3-dihydro-2H-1,3-benzamidazol-2-one | 457 | 940 | 2210 |
| 1-[4-(4-propyl-1,2-cyclohexene)-4-piperidinyl-1,3-dihydro-2H-1,3-benzamidazol-2-one | 265 | 1500 | 1220 |
| 1-[4-(4,4-difluorophenylbutyl)-4-piperidinyl]-1,3-dihydro-2H-1,3-benzamidazol-2-one | 52 | 1200 | 2050 |
| 1-[4-(4-phenyl-phenylmethyl)-4-piperidinyl]-1,3-dihydro-2H-1,3-benzamidazol-2-one | 105 | 1300 | 3290 |

What is claimed is:

1. A method of treating pain responsive to the modulation of opioid receptors, the method comprising administering to a patient in need thereof, an effective amount of a compound of formula I:

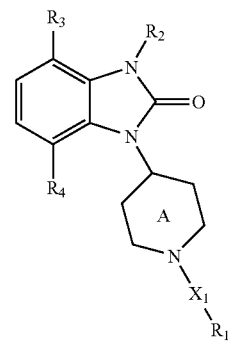

wherein
A is a saturated, unsaturated or partially unsaturated ring;
X$_1$ is selected from the group consisting of a C$_{1-10}$ branched or straight alkyl, alkenyl, alkynylene optionally substituted with 1-3 halogen, oxo or phenyl groups, said phenyl group optionally substituted with 1-3 halogen or $C_{1-10}$ alkyl groups;

$R_1$ is selected from the group consisting of $C_{3-12}$ cycloalkyl, $C_{3-12}$ cycloalkenyl, a monocyclic, bicyclic or tricyclic heteroaryl ring, a heteromonocyclic ring, and a heterobicyclic ring system, wherein said $C_{3-12}$ cycloalkyl, $C_{3-12}$ cycloalkenyl, monocyclic, bicyclic or tricyclic heteroaryl ring, heteromonocyclic ring, and heterobicyclic ring system are optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl;

$R_2$ is selected from the group consisting of $C_{1-10}$ alkyl, $C_{3-12}$ cycloalkyl and halogen, said alkyl and cycloalkyl substituted with an oxo group; and $R_3$ and $R_4$ are independently selected from the group consisting of hydrogen, hydroxy, $C_{1-3}$ alkyl, $C_{1-3}$ alkoxy, $C_{1-3}$ carbonyl and halogen; and pharmaceutically acceptable salts thereof, wherein the opioid receptors are selected from the group consisting of ORL1, μ, δ or κ receptors, and the compound of formula I has an agonistic activity at the ORL1 receptor and one or more of the μ, δ or κ receptors.

2. A method of modulating a pharmacological response from the ORL1 receptor comprising administering an effective amount of a compound of formula I:

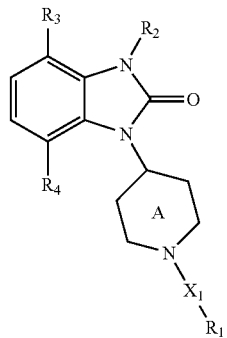

wherein

A is a saturated, unsaturated or partially unsaturated ring;

$X_1$ is selected from the group consisting of a $C_{1-10}$ branched or straight alkyl, alkenyl, alkynylene optionally substituted with 1-3 halogen, oxo or phenyl groups, said phenyl group optionally substituted with 1-3 halogen or $C_{1-10}$ alkyl groups;

$R_1$ is selected from the group consisting of $C_{3-12}$ cycloalkyl, $C_{3-12}$ cycloalkenyl, a monocyclic, bicyclic or tricyclic heteroaryl ring, a heteromonocyclic ring, and a heterobicyclic ring system, wherein said $C_{3-12}$ cycloalkyl, $C_{3-12}$ cycloalkenyl, monocyclic, bicyclic or tricyclic heteroaryl ring, heteromonocyclic ring, and heterobicyclic ring system are optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl;

$R_2$ is selected from the group consisting of $C_{1-10}$ alkyl, $C_{3-12}$ cycloalkyl and halogen, said alkyl and cycloalkyl substituted with an oxo group; and $R_3$ and $R_4$ are independently selected from the group consisting of hydrogen, hydroxy, $C_{1-3}$ alkyl, $C_{1-3}$ alkoxy, $C_{1-3}$ carbonyl and halogen; and pharmaceutically acceptable salts thereof.

3. A method of treating pain responsive to the modulation of opioid receptors, the method comprising administering to a patient in need thereof, an effective amount of a compound selected from the group consisting of 1-[4-dibenzocycloheptyl-4-piperidinyl]-1,3-dihydro-2H-1,3-benzamidazol-2-one;

1-[4-(4-propylcyclohexane)-4-piperidinyl]-1,3-dihydro-2H-1,3-benzamidazol-2-one;

1-[4-(4-propyl-1,2-cyclohexene)-4-piperidinyl-1,3-dihydro-2H-1,3-benzamidazol-2-one;

1-[4-(4,4-difluorophenylbutyl)-4-piperidinyl]-1,3-dihydro-2H-1,3-benzamidazol-2-one;

1-[4-(4-phenyl-phenylmethyl)-4-piperidinyl]-1,3-dihydro-2H-1,3-benzamidazol-2-one;

and pharmaceutically acceptable salts thereof.

4. A method of modulating a pharmacological response from the ORL1 receptor, comprising administering an effective amount of a compound selected from the group consisting of:

1-[4-dibenzocycloheptyl-4-piperidinyl]-1,3-dihydro-2H-1,3-benzamidazol-2-one;

1-[4-(4-propylcyclohexane)-4-piperidinyl]-1,3-dihydro-2H-1,3-benzamidazol-2-one;

1-[4-(4-propyl-1,2-cyclohexene)-4-piperidinyl]-1,3-dihydro-2H-1,3-benzamidazol-2-one;

1-[4-(4,4-difluorophenylbutyl)-4-piperidinyl]-1,3-dihydro-2H-1,3-benzamidazol-2-one;

1-[4-(4-phenyl-phenylmethyl)-4-piperidinyl]-1,3-dihydro-2H-1,3-benzamidazol-2-one;

and pharmaceutically acceptable salts thereof.

5. A method of modulating a response from opioid receptors comprising administering a compound of formula I:

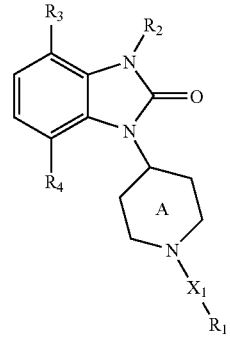

wherein

A is a saturated, unsaturated or partially unsaturated ring;

$X_1$ is selected from the group consisting of a $C_{1-10}$ branched or straight alkyl, alkenyl, alkynylene optionally substituted with 1-3 halogen, oxo or phenyl groups, said phenyl group optionally substituted with 1-3 halogen or $C_{1-10}$ alkyl groups;

$R_1$ is selected from the group consisting of $C_{3-12}$ cycloalkyl, $C_{3-12}$ cycloalkenyl, a monocyclic, bicyclic or tricyclic heteroaryl ring, a heteromonocyclic ring, and a heterobicyclic ring system, wherein said $C_{3-12}$ cycloalkyl, $C_{3-12}$ cycloalkenyl, monocyclic, bicyclic or tricyclic heteroaryl ring, heteromonocyclic ring, and heterobicyclic ring system are optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl;

$R_2$ is selected from the group consisting of $C_{1-10}$ alkyl, $C_{3-12}$ cycloalkyl and halogen, said alkyl and cycloalkyl substituted with an oxo group; and $R_3$ and $R_4$ are independently selected from the group consisting of hydrogen, hydroxy, $C_{1-3}$ alkyl, $C_{1-3}$ alkoxy, $C_{1-3}$ carbonyl and halogen; and pharmaceutically acceptable salts thereof;

the compound having a binding affinity for the ORL1 receptor of less than 500 $K_i$ (nM) and a binding affinity for the μ receptor of less than 25 $K_i$ (nM).

6. A method of reducing side effects associated with the administration of opioid analgesics in a human patient comprising administering to said human patient an analgesically effective amount of a non-opioid compound of formula I:

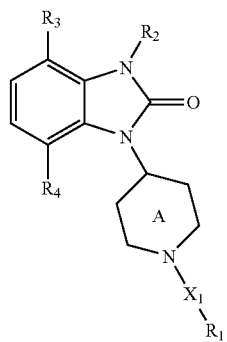

wherein

A is a saturated, unsaturated or partially unsaturated ring;

$X_1$ is selected from the group consisting of a $C_{1-10}$ branched or straight alkyl, alkenyl, alkynylene optionally substituted with 1-3 halogen, oxo or phenyl groups, said phenyl group optionally substituted with 1-3 halogen or $C_{1-10}$ alkyl groups;

$R_1$ is selected from the group consisting of $C_{3-12}$ cycloalkyl, $C_{3-12}$ cycloalkenyl, a monocyclic, bicyclic or tricyclic heteroaryl ring, a heteromonocyclic ring, and a heterobicyclic ring system, wherein said $C_{3-12}$ cycloalkyl, $C_{3-12}$ cycloalkenyl, monocyclic, bicyclic or tricyclic heteroaryl ring, heteromonocyclic ring, and heterobicyclic ring system are optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl;

$R_2$ is selected from the group consisting of $C_{1-10}$ alkyl, $C_{3-12}$ cycloalkyl and halogen, said alkyl and cycloalkyl substituted with an oxo group; and $R_3$ and $R_4$ are independently selected from the group consisting of hydrogen, hydroxy, $C_{1-3}$ alkyl, $C_{1-3}$ alkoxy, $C_{1-3}$ carbonyl and halogen; and pharmaceutically acceptable salts thereof;

wherein the compound exhibits a binding affinity for the ORL1 opioid receptor of less than 500 $K_i$ (nM), and the side effects being reduced are selected from the group consisting of respiratory depression, constipation and development of tolerance and dependence.

7. The method of claim 6 wherein said compound has a binding affinity for the μ opioid receptor of less than 25 $K_i$ (nM).

8. The method of claim 1, wherein $R_1$ is a $C_{3-12}$ cycloalkyl which is optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl.

9. The method of claim 1, wherein the compound of formula I is selected from the group consisting of:

1-[1-dibenzocycloheptyl-4-piperidinyl]-3-[1-oxo-ethyl]-1,3-dihydro-2H-1,3-benzamidazol-2-one;

1-[1-(4-propylcyclohexane)-4-piperidinyl]-3-[1-oxo-propyl]-1,3-dihydro-2H-1,3-benzamidazol-2-one;

1-[1-(4-propylcyclohexane)-4-piperidinyl]-3-[1-oxo-ethyl]-1,3-dihydro-2H-1,3-benzamidazol-2-one;

1-[1-(4-propylcyclohexane)-4-piperidinyl]-3-[2-oxo-cyclopropyl]-1,3-dihydro 2H-1,3-benzamidazol-2-one;

1-[1-cyclodecyl-4-piperidinyl]-3-[1-oxo-ethyl]-1,3-dihydro-2H-1,3-benzamidazol-2-one;

1-[1-(cyclooctylmethyl)-4-piperidinyl]-3-[1-oxo-ethyl]-1,3-dihydro-2H-1,3-benzamidazol-2-one; and pharmaceutically acceptable salts thereof.

10. The method of claim 2, wherein $R_1$ is a $C_{3-12}$ cycloalkyl which is optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl.

11. The method of claim 2, wherein the compound of formula I is selected from the group consisting of:

1-[1-dibenzocycloheptyl-4-piperidinyl]-3-[1-oxo-ethyl]-1,3-dihydro-2H-1,3-benzamidazol-2-one;

1-[1-(4-propylcyclohexane)-4-piperidinyl]-3-[1-oxo-propyl]-1,3-dihydro-2H-1,3-benzamidazol-2-one;

1-[1-(4-propylcyclohexane)-4-piperidinyl]-3-[1-oxo-ethyl]-1,3-dihydro-2H-1,3-benzamidazol-2-one;

1-[1-(4-propylcyclohexane)-4-piperidinyl]-3-[2-oxo-cyclopropyl]-1,3-dihydro-2H-1,3-benzamidazol-2-one;

1-[1-cyclodecyl-4-piperidinyl]-3-[1-oxo-ethyl]-1,3-dihydro-2H-1,3-benzamidazol-2-one;

1-[1-(cyclooctylmethyl)-4-piperidinyl]-3-[1-oxo-ethyl]-1,3-dihydro-2H-1,3-benzamidazol-2-one; and pharmaceutically acceptable salts thereof.

12. The method of claim 5, wherein $R_1$ is a $C_{3-12}$ cycloalkyl which is optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl.

13. The method of claim 5, wherein the compound of formula I is selected from the group consisting of:

1-[1-dibenzocycloheptyl-4-piperidinyl]-3-[1-oxo-ethyl]-1,3-dihydro-2H-1,3-benzamidazol-2-one;

1-[1-(4-propylcyclohexane)-4-piperidinyl]-3-[1-oxo-propyl]-1,3-dihydro-2H-1,3-benzamidazol-2-one;

1-[1-(4-propylcyclohexane)-4-piperidinyl]-3-[1-oxo-ethyl]-1,3-dihydro-2H-1,3-benzamidazol-2-one;

1-[1-(4-propylcyclohexane)-4-piperidinyl]-3-[2-oxo-cyclopropyl]-1,3-dihydro-2H-1,3-benzamidazol-2-one;

1-[1-cyclodecyl-4-piperidinyl]-3-[1-oxo-ethyl]-1,3-dihydro-2H-1,3-benzamidazol-2-one;

1-[1-(cyclooctylmethyl)-4-piperidinyl]-3-[1-oxo-ethyl]-1,3-dihydro-2H-1,3-benzamidazol-2-one; and pharmaceutically acceptable salts thereof.

14. The method of claim 6, wherein $R_1$ is a $C_{3-12}$ cycloalkyl which is optionally substituted with 1-3 substituents selected from the group consisting of halogen, $C_{1-10}$ alkyl, nitro, trifluoromethyl, phenyl, benzyl, phenyloxy and benzyloxy, wherein said phenyl, benzyl, phenyloxy and benzyloxy are optionally substituted with halogen or $C_{1-10}$ alkyl.

15. The method of claim 6, wherein the compound of formula I is selected from the group consisting of:

1-[1-dibenzocycloheptyl-4-piperidinyl]-3-[1-oxo-ethyl]-1,3-dihydro-2H-1,3-benzamidazol-2-one;

1-[1-(4-propylcyclohexane)-4-piperidinyl]-3-[1-oxo-propyl]-1,3-dihydro-2H-1,3-benzamidazol-2-one;

1-[1-(4-propylcyclohexane)-4-piperidinyl]-3-[1-oxo-ethyl]-1,3-dihydro-2H-1,3-benzamidazol-2-one;

1-[1-(4-propylcyclohexane)-4-piperidinyl]-3-[2-oxo-cyclopropyl]-1,3-dihydro-2H-1,3-benzamidazol-2-one;

1-[1-cyclodecyl-4-piperidinyl]-3-[1-oxo-ethyl]-1,3-dihydro-2H-1,3-benzamidazol-2-one;

1-[1-(cyclooctylmethyl)-4-piperidinyl]-3-[1-oxo-ethyl]-1,3-dihydro-2H-1,3-benzamidazol-2-one; and pharmaceutically acceptable salts thereof.

\* \* \* \* \*